(12) United States Patent
McMinn (10) Patent No.: US 9,427,323 B2
(45) Date of Patent: *Aug. 30, 2016

(54) KNEE PROSTHESIS

(71) Applicant: Derek J. W. McMinn, West Midlands (GB)

(72) Inventor: Derek J. W. McMinn, West Midlands (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,277

(22) Filed: Jan. 7, 2015

(65) Prior Publication Data

US 2015/0190235 A1 Jul. 9, 2015

(30) Foreign Application Priority Data

Jan. 7, 2014 (GB) .................................. 1400224.0

(51) Int. Cl.
*A61F 2/38* (2006.01)
*A61F 2/30* (2006.01)

(52) U.S. Cl.
CPC ............. *A61F 2/3859* (2013.01); *A61F 2/389* (2013.01); *A61F 2/3886* (2013.01); *A61F 2002/30224* (2013.01); *A61F 2002/30289* (2013.01); *A61F 2250/006* (2013.01)

(58) Field of Classification Search
CPC .................................................... A61F 2/3886
See application file for complete search history.

(56) References Cited

U.S. PATENT DOCUMENTS

| | | | |
|---|---|---|---|
| 3,748,662 A | 7/1973 | Helfet | |
| 4,057,858 A | 11/1977 | Helfet | |
| 5,219,362 A * | 6/1993 | Tuke | A61F 2/38 623/20.31 |
| 6,846,329 B2 * | 1/2005 | McMinn | A61F 2/3886 623/20.14 |
| 2003/0153979 A1 * | 8/2003 | Hughes | A61F 2/30767 623/20.28 |
| 2010/0191341 A1 * | 7/2010 | Byrd | A61F 2/38 623/20.3 |

FOREIGN PATENT DOCUMENTS

| | | |
|---|---|---|
| GB | 2223950 A | 4/1990 |
| GB | 2387546 A | 10/2003 |

OTHER PUBLICATIONS

Search Report Received for GB Patent Application No. 1400224.0, mailed on Aug. 11, 2014, 1 page.

* cited by examiner

*Primary Examiner* — Thomas J Sweet
*Assistant Examiner* — Megan Wolf
(74) *Attorney, Agent, or Firm* — Morgan, Lewis & Bockius LLP (57) ABSTRACT

A knee prosthesis comprises a femoral component for securement to a femur, the femoral component defining medial and lateral condyles and an intercondylar groove; and a tibial component for securement to a tibia, the tibial component having respective bearing surfaces shaped to engage with said condyles both when the knee, in use, is extended and also over a range of flexion. At least one of the condyles is part-helical in shape and the respective bearing surface of the tibial component is correspondingly part-helical in at least a medio-lateral direction. In addition, the other bearing surface is incongruent with the other condyle in at least the antero-posterior direction so as to allow for antero-posterior movement of the femoral component relative to the bearing surfaces of the tibial component.

17 Claims, 9 Drawing Sheets

KNEE PROSTHESIS

RELATED APPLICATION

This application claims priority to United Kingdom Patent Application No. 1400224.0, filed on Jan. 7, 2014, the entire disclosure of which is incorporated by reference herein.

FIELD OF THE INVENTION

This invention relates to a knee prosthesis for fitting to a patient as a replacement knee joint.

BACKGROUND TO THE INVENTION

In a normal knee, the groove on the femur for the patella is laterally displaced with respect to the mid-point of the femur, this lateral displacement being of the order of 5 mm. In addition to being laterally displaced, the patella groove on the femur is laterally angulated by 7° with respect to the distal femur and knee joint.

In the normal knee therefore as it flexes, the patella articulates in the patella groove on the femur. Clearly it is thus important in knee replacement design to reproduce the natural position of the patella groove on the prosthetic femoral component. This is not presently reliably reproduced in many knee replacement designs, and lateral patella maltracking is a common cause of pain and morbidity. In one known design, part of the lateral femoral condyle prosthesis is removed to accommodate such lateral displacement of the groove. This is undesirable in producing a reduced area of contact between the lateral femoral condyle and the polyethylene articulating surface, with the potential for increased plastics wear.

In another known design the long axis of the femoral condyles is at right angles to the transverse axis of the knee joint. When the knee is extended, the patella articulates at the front of the femoral component. Since this area is not required for the tibia-femoral articulation, then metal can be removed to provide a lateral angulation to the patella groove. However, when the knee is flexed, the patella groove is the general area between the medial and lateral femoral condyles, and these condyles are involved in the tibia-femoral articulation in extension. Any attempt by a designer to angulate the patella groove will have serious detrimental effects. The more the patella groove is angulated and displaced, the more the area of articulation for the lateral femoral condyle is reduced.

In GB2387546B the Applicant proposed a new design of knee prosthesis to address the problems with the above. This design includes a mobile bearing component between the femoral and tibial components, the bearing component having respective surfaces shaped to match the femoral condyles and engage therewith both when the knee is extended and also over a range of flexion. The condyles are in the form of respective parts of a common helix and the respective matching surfaces of the bearing component are correspondingly part-helical. Although this design represents an improvement over the above and provides a high level of congruity at the femoro-meniscal joint, the design also requires that the bearing component is mobile with respect to the tibial component so as to allow for rotation of the knee and this can have attendant drawbacks in terms of complexity of design and surgical implantation as well as cost.

An object of the present invention is therefore to provide an improved knee prosthesis which reduces or obviates the disadvantages of the prior art referred to.

SUMMARY OF THE INVENTION

According to the present invention there is provided a knee prosthesis comprising:
- a femoral component for securement to a femur, the femoral component defining medial and lateral condyles and an intercondylar groove; and
- a tibial component for securement to a tibia, the tibial component having respective bearing surfaces shaped to engage with said condyles both when the knee, in use, is extended and also over a range of flexion;
- at least one of the condyles being part-helical in shape and the respective bearing surface of the tibial component being correspondingly part-helical in at least a medio-lateral direction; and
- wherein the other bearing surface is incongruent with the other condyle in at least the antero-posterior direction so as to allow for antero-posterior movement of the femoral component relative to the bearing surfaces of the tibial component.

Embodiments of the present invention therefore provide a knee prosthesis which, due to the presence of at least one helical condyle rotating in a medio-lateral conforming bearing surface, provides the desired lateral translation of the intercondylar groove when the knee is flexed, therefore ensuring correct patellar tracking. However, unlike in GB2387546B, the present design does not require a mobile bearing component in order to allow rotation of the knee. Instead, the present knee prosthesis includes bearing surfaces which are fixed with respect to the tibial component and wherein the required antero-posterior movement is permitted by the incongruent nature of the other condyle. The fixed bearing therefore negates the complexities of implanting a mobile bearing design, as in the prior art, whilst retaining the advantages of correct patella tracking.

However, it is not possible to have a fixed bearing design with highly conforming congruent bearing surfaces which match helical condyles on both the lateral and medial side since the knee would not be permitted to rotate and such a design would generate forces that would loosen the components. Thus, instead of a mobile bearing with congruent contact between the femoral component and the meniscus bearing component, the present invention provides a fixed bearing, without a separate meniscal component, and incongruent contact between the femoral component and the tibial component.

Flexion of the knee, in use, from an extended position may induce lateral translatory movement of the femoral component upon the tibial component. The lateral translatory movement may be 3.5 mm per 90° of flexion.

In certain embodiments, at least one of the condyles may have point or line contact, as opposed to area contact, with a respective bearing surface.

At least the bearing surfaces of the tibial component may comprise a polymer, preferably a cross-linked polymer. For example, the bearing surfaces may comprise polyethylene, preferably, UHMWPE and, more preferably, cross-linked UHMWPE. The tibial bearing surface may comprise a hybrid polyethylene component where the bulk of the component is conventional polyethylene to retain strength and the bearing surface only is cross-linked polyethylene to give wear resistance as disclosed in GB2387546B. The lack of area contact between the femoral component and the tibial component can therefore be compensated for by improved wear characteristics arising from cross-linking of the bearing surfaces.

The at least one condyle may be shaped in the manner of the threads on a screw, and the respective bearing surface may be shaped in the manner of threads cut in a complementary nut. However, the respective bearing surface could be in the manner of the threads on the screw, with the at least one condyle shaped in the manner of the threads cut in the nut.

The medial and lateral condyles may have the same shapes or may be differently shaped. For example, the medial and lateral condyles may both be part-helical in shape (e.g. the condyles may be in the form of respective parts of a common helix). Alternatively, one condyle may be non-helical.

In particular embodiments, at least the medial condyle is part-helical in shape.

In a specific embodiment, the knee prosthesis may be configured as a medially pivoting knee. In which case, the medial condyle is part-helical in shape and is configured for congruent (area) contact with a respective bearing surface which is correspondingly part-helical in both the medio-lateral direction and the antero-posterior direction. The lateral condyle in this embodiment may also be part-helical. In which case, the respective bearing surface for the lateral condyle will be configured for incongruent (line or point) contact and may be part-helical in the medio-lateral direction only (i.e. to form a trough) or may be planar or curved. Alternatively, the lateral condyle may be non-helical and the respective bearing surface may be planar or curved and may be configured for incongruent contact in both the antero-posterior direction and the medio-lateral direction. It will be understood that the incongruent contact between the lateral condyle and the respective bearing surface allows the required antero-posterior movement of the femoral component upon rotation of the knee. In this particular embodiment, the femoral component is allowed to rotate around the medial femoro-tibial articulation with antero-posterior movement at the lateral femoro-tibial articulation. The reverse arrangement is also possible with a helical near conforming lateral femoro-tibial articulation providing desirable lateral femoral translation with increasing knee flexion and rotation being allowed for with an incongruent medial femoro-tibial articulation giving antero-posterior movement.

In another embodiment, the knee prosthesis may be configured as a so-called Total Condylar Design such that the intact posterior cruciate ligament causes roll-back of the femoral component on the tibial component with increasing flexion. In this case, the medial condyle, the lateral condyle or both condyles may be part helical in shape. However, unlike for the above embodiment, in this case, each of the bearing surfaces must be configured for incongruent contact with the respective condyles in the antero-posterior direction so as to allow for the femoral component to freely slide back and forth on the tibial component during flexion and extension. It will be understood that any constraint in the antero-posterior direction as a result of the shapes of the bearing surfaces, will cause conflict with the movement dictated by the posterior cruciate ligament with resultant component loosening and/or component breakage, hence the need for complete incongruent contact in the antero-posterior direction, in this embodiment. However, in order to ensure that lateral translation of the intercondylar groove is maintained, at least one of the condyles must be part-helical and the respective bearing surface of the tibial component must be correspondingly part-helical in the medio-lateral direction only (i.e. the respective bearing surface should be in the form of a trough, giving side-to-side conformity and normal translation, but offering no front-to-back constraint). A single part-helical condyle articulating in such a medio-laterally constrained bearing surface is believed to be sufficient to provide the desired lateral translation.

As above, the other condyle in this embodiment may either be part-helical or non-helical. If the other condyle is part-helical the respective bearing surface may or may not be similarly helical in the medio-lateral direction. If the other femoral condyle is non-helical, the respective bearing surface must not constrain the movement of the other condyle in the medio-lateral direction since any such constraint would result in a conflict which would likely result in breakage or severe wear. For example, the helical condyle in its medio-laterally constrained trough will try to cause lateral translation, but if the non-helical other condyle is also constrained medio-laterally it will try to prevent any lateral translation.

In another embodiment, the knee prosthesis may be configured as a so-called Posterior Stabilised Design where there is no functioning posterior cruciate ligament but, at increasing flexion (e.g. at approximately 80 degrees of flexion), a peg and cam mechanism are designed to engage to cause roll-back of the femoral component on the tibial component. Thus, the condyles and bearing surfaces must essentially be designed as per the Total Condylar Design described above so as to ensure that there is no constraint on antero-posterior movement when the peg and cam are engaged. In such embodiments, the knee prosthesis may be configured substantially in line with the applicants' earlier GB2426201 with the condyles and bearing surfaces being adapted in line with the present invention. Again at least one femoral condyle is part helical with medio-lateral engagement with its respective tibial bearing surface to generate desirable femoral translation with knee flexion.

The transverse cross-section of each condyle may be flat, curved or semi-spherical and may be the same or different for each condyle.

The tibial component may be constituted by a single component, which may be all polyethylene, or a multi-part component. For example, the tibial component may comprise a bearing component comprising the bearing surfaces and an engaging (tibial baseplate) component comprising an engagement feature for securing the tibial component to a patient's tibia. The bearing component may be configured for snap-fit engagement with the engaging component, or may be manufactured fitted to the tibial baseplate. The bearing component may be formed from a polymer, preferably a cross-linked polymer. For example, bearing component may be formed from polyethylene, preferably, UHMWPE and, more preferably, cross-linked UHMWPE, and more preferably hybrid polyethylene. The tibial baseplate may commonly be formed from a metal, but could also be formed from a tough polymer such as PEEK (polyether ether ketone). For example, engaging component may be formed from polyethylene, preferably, UHMWPE and, more preferably, cross-linked UHMWPE. Alternatively, the engaging component may be formed from metal.

BRIEF DESCRIPTION OF THE DRAWINGS

The invention will now be described, by way of example, with reference to the accompanying drawings, in which.

DETAILED DESCRIPTION OF SPECIFIC EMBODIMENTS

As will be described in relation to the knee prosthesis shown in the accompanying Figures, embodiments of the present invention generally relate to the shaping of at least one of the medial and lateral condyles and the engagement with a corresponding bearing surface of the tibial component, for example in the manner of a screw-thread and associated corresponding nut engaged therewith. Although it would be possible to provide condyles in the form of the threads cut in the nut, with the threads on the screw being provided by the bearing surfaces, it is preferred, as will be described, that the screw-threads, i.e. the male part of the thread will be defined by the at least one condyle, with the bearing surface being correspondingly grooved in the nature of the threads cut in the nut. By this means, as will be more fully explained below, lateral translation of the femoral component can be realised without requiring a mobile bearing component to accommodate antero-posterior movement as the knee is flexed.

Figure 1:
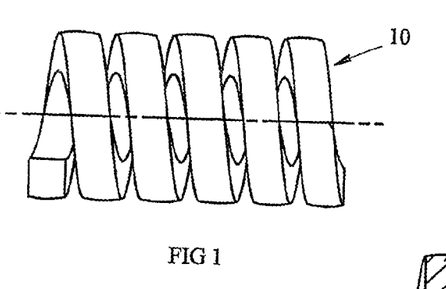
FIGS. 1 to 3 are schematic explanatory views relating to the formation of one or more helical condyles of a femoral component of a knee prosthesis according to embodiments of the present invention.
Figure 2:
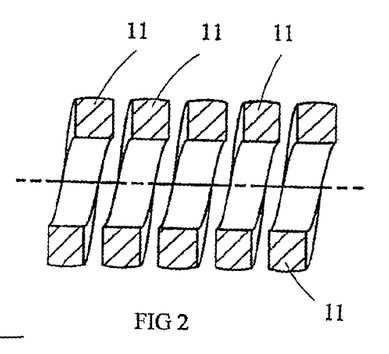

FIGS. 1 to 4A schematically show the form of the helical nature of the femoral condyles and the grooves in a tibial bearing component according to an embodiment of the invention. FIG. 1 shows a helix 10 with a certain selected angle defining the pitch of the thread. FIG. 2 shows a section through the helix of FIG. 1 so as to define a series of spaced part-helical forms 11. It will be understood how two of these can be adapted to form the shape of the respective sections 12, 13 shown in FIG. 3 which approximate to the condylar sections of a femoral component to be described in relation to the drawings showing the assembled prosthesis. However, it will also be understood that embodiments of the present invention may include only one such helical condyle 12, 13 with the other condyle being non-helical, for example, circular.

Medial Rotating Design

Figure 4A:
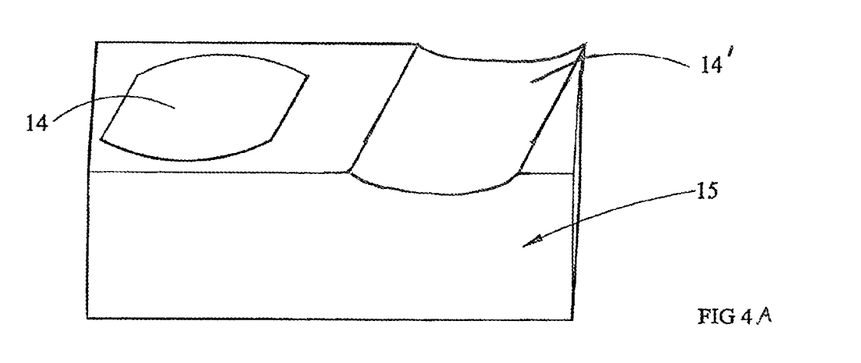
FIGS. 4A and 4B are further schematic, explanatory views showing the formation of part-helical grooves constituting bearing surfaces of a tibial component for a knee prosthesis according to embodiments of the present invention.

A further illustration of the nature of the part-helical arrangement of a prosthesis according to an embodiment of the present invention is shown in FIG. 4A in relation to the shapes of the respective grooves or bearing surfaces 14, 14' formed in the tibial component which is schematically shown in the form of a block 15. It can be seen that each groove is at an angle to the longitudinal extent of the block, this angle corresponding to the angle of the helix 10 shown in FIG. 1, with the two part-helical sections 12, 13 of the helix 10 corresponding respectively in at least the (transverse) medio-lateral direction with the grooves 14, 14' of the tibial component. More specifically, the medial bearing surface 14 is shaped to conform exactly with the medial condyle 12 so as to produce congruent area contact in both the medio-lateral direction and the antero-posterior direction (i.e. the surface 14 is curved both side-to-side and front-to-back). On the other hand, the lateral bearing surface 14' is shaped only to conform with the lateral condyle 13 in the medio-lateral direction so as to produce incongruent line contact (i.e. the surface 14' is curved side-to-side but straight front-to-back). It will be understood that such a configuration will allow a femoral component comprising the condyles 12, 13 to rotate on the tibial component 15, thereby permitting antero-posterior movement when the condyles 12, 13 are engaged in the bearing surfaces 14, 14'.

Figure 4B:
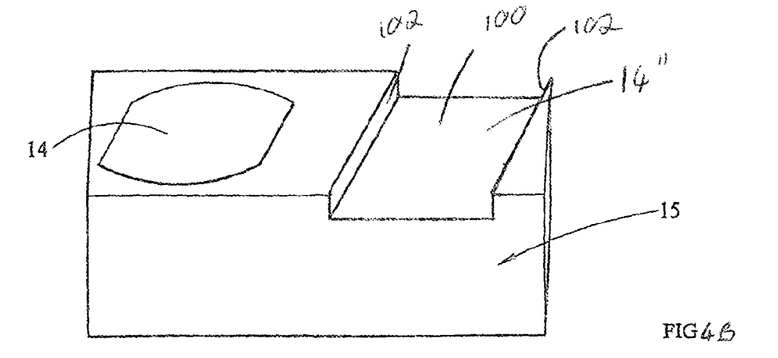

FIG. 4B shows an alternative schematic tibial component 15 in which the medial bearing surface 14 is the same as in FIG. 4A but wherein the groove constituting the lateral bearing surface 14" has been squared off to comprise a flat base 100 and two opposed perpendicular side walls 102. However, the angle of the groove 14" has not been altered and is consistent with both the angle of the groove 14 and the angle of each of the part-helical condyles 12, 13. Since the condyles 12, 13 have a curved transverse cross-section, in this embodiment, the lateral condyle 13 will only make point contact with the base 100 of groove 14". However, as above, antero-posterior movement of the femoral component is permitted since there is no antero-posterior constraint imposed on the lateral condyle 13 by the surface 14".

Figure 3:
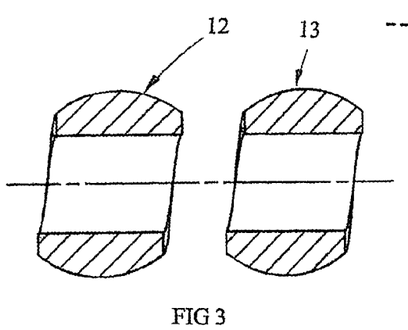
Figure 5:
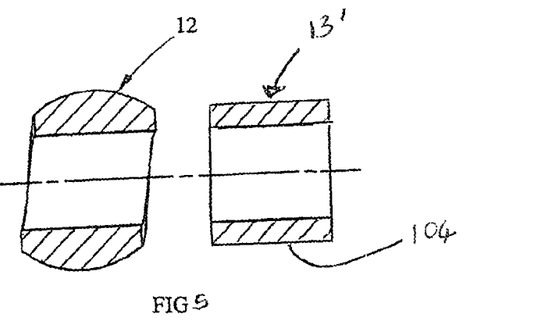
FIG. 5 is view similar to that of FIG. 3 but wherein only one condyle is part-helical and the other condyle is circular, having a flat engagement surface in accordance with an embodiment of the present invention.

FIG. 5 shows a view similar to that of FIG. 3 but wherein only one condyle 12 is part-helical and the other condyle 13' is circular, having a flat engagement surface 104 in accordance with an embodiment of the present invention.

Figure 6:
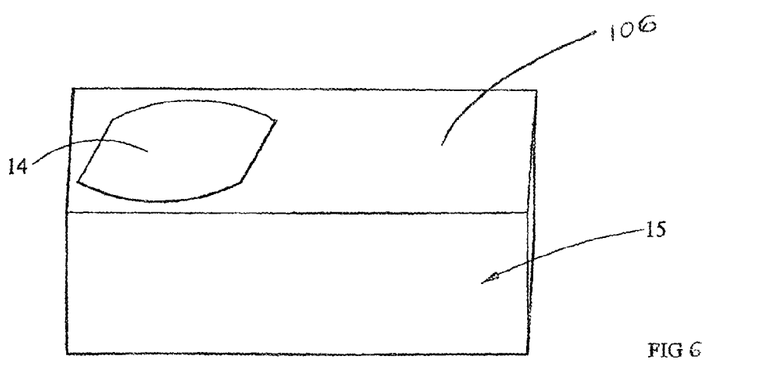
FIGS. 6 to 9 are further schematic, explanatory views showing the formation of various bearing surfaces of a tibial component for a knee prosthesis according to embodiments of the present invention.

FIG. 6 shows a further schematic tibial component 15 which has been configured for use with the condyles 12, 13' of FIG. 5. Thus, tibial component 15 comprises a medial bearing surface 14 which is the same as in FIGS. 4A and 4B but wherein no groove is provided on the lateral side and, instead, the lateral side of the tibial component 15 has a planar surface constituting a lateral bearing surface 106 for engagement with the lateral condyle 13'. It will be understood that, when the condyles 12, 13' of FIG. 5 are engaged with the tibial component 15 of FIG. 6, area contact will be achieved on the medial side and line contact will be achieved on the lateral side. Furthermore, the helical medial condyle 12 will induce a lateral translation of the femoral component while the lateral condyle 13' will be allowed to move in an antero-posterior direction to permit rotation of the femoral component with respect to the tibial component 15.

Total Condylar Design

Figure 7:
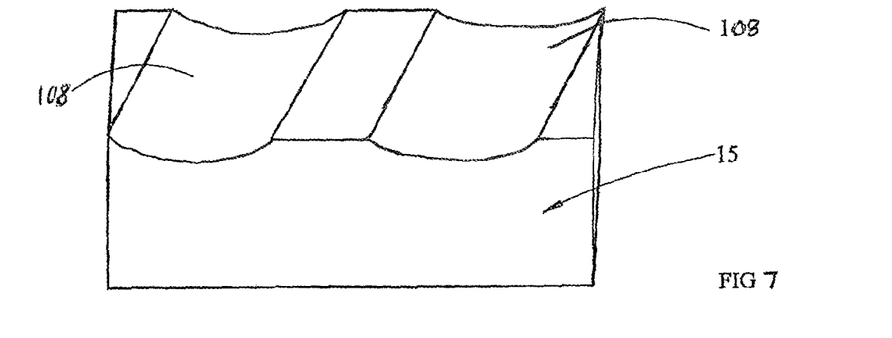

FIG. 7 shows a further schematic tibial component 15 which has been configured for use with the condyles 12, 13 of FIG. 3 in accordance with another embodiment of the invention. In this case, each of the grooves 108 constituting the bearing surfaces are configured as per the lateral bearing surface 14' of FIG. 4A. Thus, the bearing surfaces 108 are shaped only to conform with the lateral condyle 13 in the medio-lateral direction so as to produce incongruent line contact (i.e. the surfaces 108 are curved side-to-side but straight, albeit angled, front-to-back). This embodiment, therefore allows each condyle to move in an antero-posterior direction upon knee rotation, for example, so as to allow for the action of an intact posterior cruciate ligament pulling the femoral component backwards as the knee is flexed.

Figure 8:
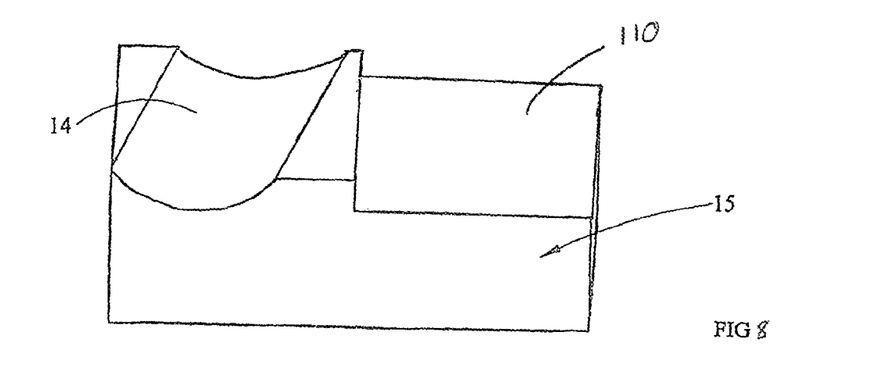

FIG. 8 shows another schematic tibial component 15, which is similar to that in FIG. 7 but wherein the top portion of the lateral side of the tibial component 15 has been removed to form a sunken planar bearing surface 110. As above, this tibial component 15 may be used alongside the condyles 12, 13 of FIG. 3 such that the medial condyle 12 causes lateral translation of the femoral component and both the medial and lateral condyles 12, 13 are free to move in an antero-posterior direction.

Figure 9:
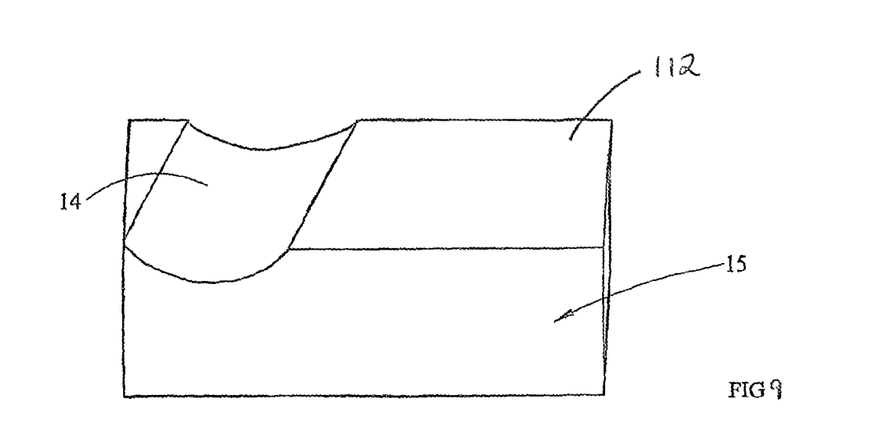

FIG. 9 shows a still further schematic tibial component 15, which is similar to that in FIG. 8 but wherein the top portion of the lateral side of the tibial component 15 is maintained and is formed into a planar bearing surface 112 similar to that of FIG. 6. Accordingly, this tibial component 15 may be used with the condyles 12, 13' of FIG. 5 in a similar manner to that described above in relation to FIG. 8.

Figure 10A:
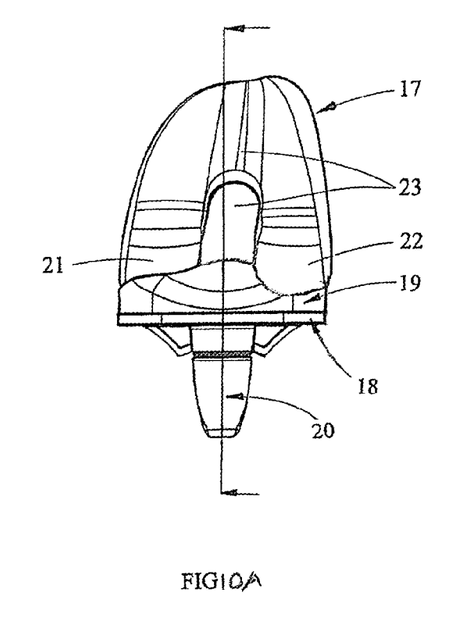
FIGS. 10A to 10C show respectively, a front, medial side and lateral side view of a prosthesis according to an embodiment of the present invention, with the knee in a partly flexed state.
Figure 10B:
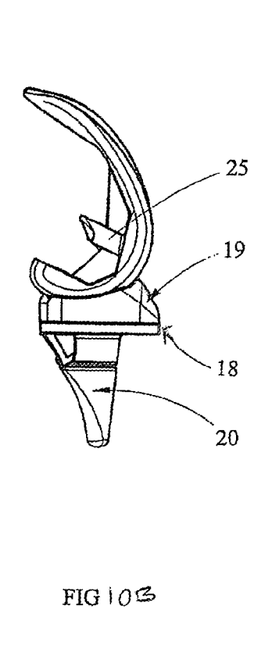
Figure 10C:
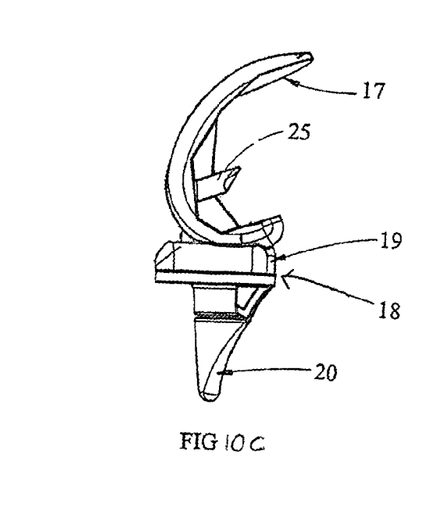
Figure 11A:
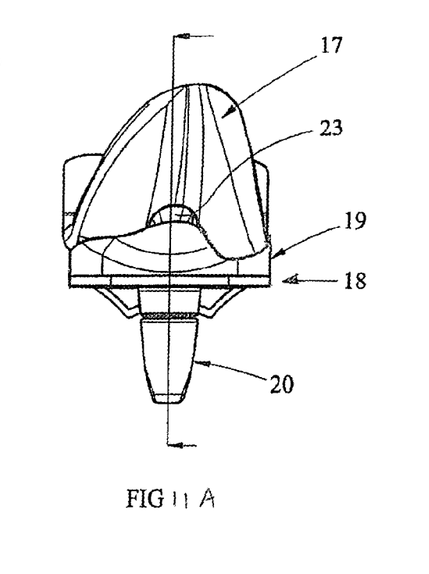
FIGS. 11A and 11B show respectively, a front and medial side view of the prosthesis of FIGS. 10A through 10C, with the knee in an extended state.
Figure 11B:
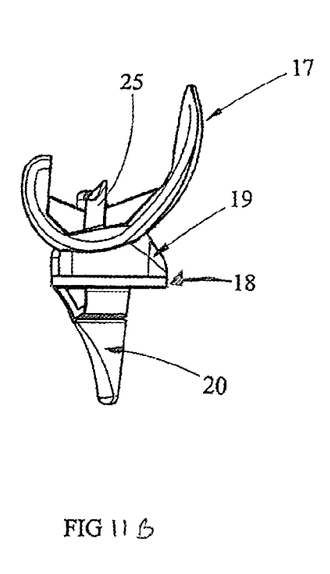

FIGS. 10A through 11B show an assembled prosthesis comprising a femoral component 17 and a tibial component 18. The tibial component 18 is comprised of a fixed bearing component 19 disposed on an engaging component in the form of a stabilising peg 20. It is intended that in use the femoral component 17 is secured to the end of the femur from which bone has appropriately been removed. The femoral component 17 can be fixed in any suitable manner. The peg 20 is, in use, secured to the top of the tibia, again in any suitable manner. Whilst FIGS. 10A to 10C show the prosthesis in a state equivalent to one fitted to a partly flexed knee, FIGS. 11A and 11B show the state when it is fitted to a knee which is extended.

Figure 12A:
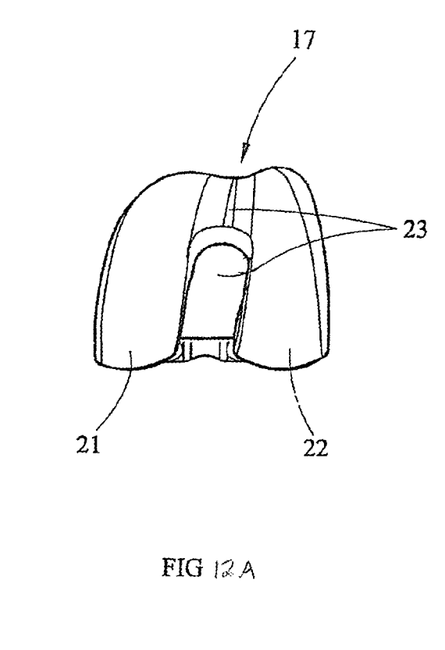
FIGS. 12A to 12C show respectively a front, side and rear view of a femoral component of a knee prosthesis according to embodiments of the present invention.
Figure 12B:
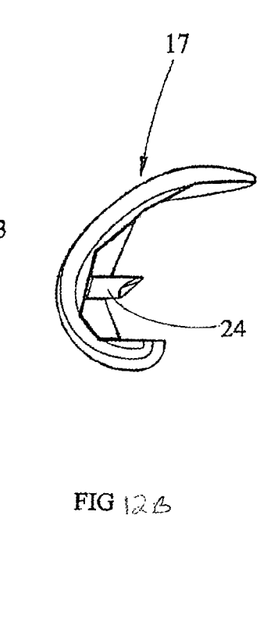
Figure 12C:
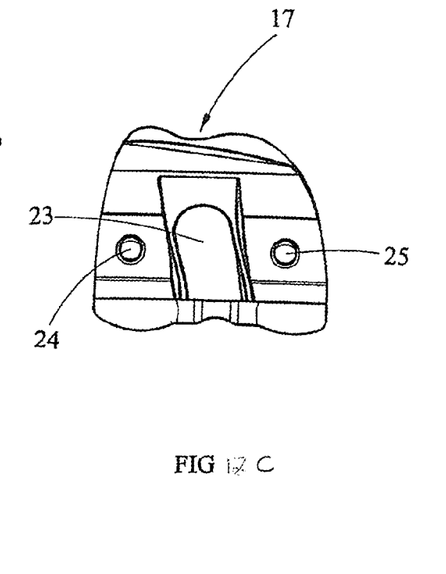

The femoral component 17 is shown in more detail in FIGS. 12A through 12C and is of a generally known form defining outer generally arcuate medial condylar and lateral condylar surfaces 21, 22 respectively. In this embodiment, the condyles 21, 22 are shaped similarly to those shown in FIG. 3, in the manner of screw-threads, i.e. are each part-helical, being formed from the same helix. Defined between and parallel to the medial and lateral condyles is the inter-condylar (patella) groove 23. From FIGS. 10A and 11A, for example, it will be appreciated that the helical nature of the condyles 21, 22 results in the patellar-femoral articulation being displaced laterally with respect to the mid-point of the tibial-femoral articulation as the knee rotates. The patella groove is thus laterally displaced, the amount of lateral displacement depending upon the pitch of the 'threads' which the condyles define.

From FIGS. 12B and 12C it can be seen that at the interior surface of the femoral component 17, at respective opposite sides of the patella groove are respective pegs 24, 25 to facilitate fixing of the femoral component 17 to the end of the femur, in use.

Figure 13A:
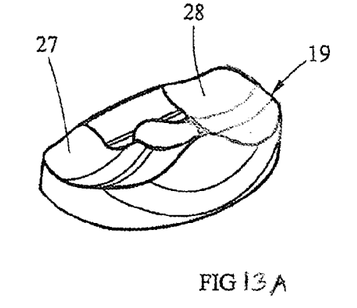
FIGS. 13A to 13C show respectively a perspective, plan and side view of a bearing component of a tibial component of a knee prosthesis according to embodiments of the present invention.
Figure 13B:
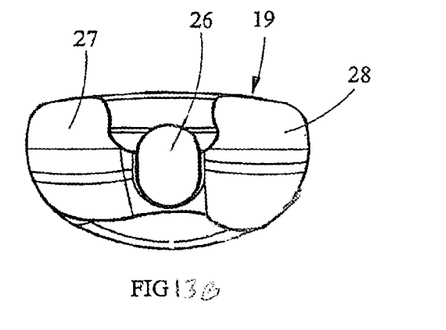
Figure 13C:
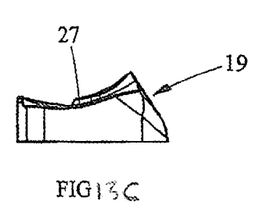

FIGS. 13A to 13C show the bearing component 19, which has a raised central area 26 between bearing surfaces 27, 28. In this particular embodiment, the bearing surfaces 27, 28 are similar to those of FIG. 4A in that the medial bearing surface 27 is shaped to conform exactly with the medial condyle 21 so as to produce congruent area contact in both the medio-lateral direction and the antero-posterior direction while the lateral bearing surface 28 is shaped only to conform with the lateral condyle 22 in the medio-lateral direction so as to produce incongruent line contact and to allow antero-posterior movement. In other embodiments, the bearing surfaces may be configured as per those shown in the other schematic illustrations of the tibial component 15.

Figure 14A:
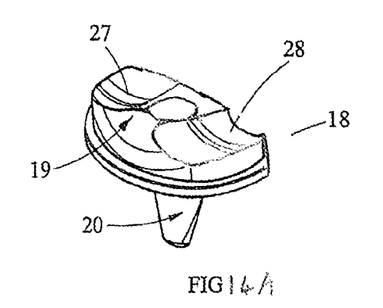
FIGS. 14A to 14C show respectively a perspective, front and plan view of a tibial component including the bearing component of FIGS. 13A to 13C.
Figure 14B:
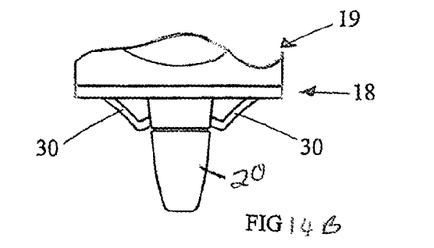
Figure 14C:
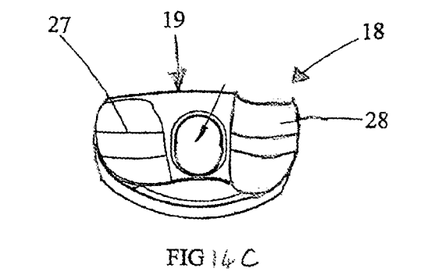

As shown in FIGS. 14A through 14C, the bearing component 19 is snap-fitted onto the engaging component and the peg 20 is provided with ribs 30 to assist fixing of the tibial component 18 to the tibia, in use.

It will be appreciated that the femoral component 17 would normally be of metallic material with its condylar surfaces 21, 22 highly polished. Typically, it could be of cobalt chrome and would be affixed to the femur by any form of suitable cement adhesion or biological fixation. Similarly, the engaging component 20 would also normally be of metallic material, again such as cobalt chrome. However, the bearing component 19 preferably comprises cross-linked Ultra High Molecular Weight Polyethylene (UHMPE) at least for its bearing surfaces 27, 28.

It is believed that it will be appreciated from the above, in conjunction with FIGS. 10A through 11B how the prosthesis of the present embodiment operates, in use.

As described above, the helical form of at least one of the condyles of the femoral component serves to displace the patella groove laterally. This is a static effect, with the amount of lateral displacement being proportional to the angle of the helix. Additionally, the helical arrangement means that the 'helix' advances when turned relative to the bearing component 19. Accordingly when the knee is flexed, in use, from an extended position, the helical nature of the at least one condyle induces a lateral translatory movement of the femoral component, and thus of the femur, upon the tibial component 18. This is a dynamic effect corresponding to the turning of a thread relative to a fixed nut. This again is desirable because the whole of the femur, and thus the patella groove also, is moved laterally with increasing flexion of the knee. However, it also a feature of the present invention that at least one of the condyles is unconstrained in at least an antero-posterior direction. This allows the femoral component to shift backwards with respect to the tibial component and, in some embodiments, allows rotation of the femoral component around the tibial axis, without the need for a rotating platform design as in the prior art.

Figure 15A:
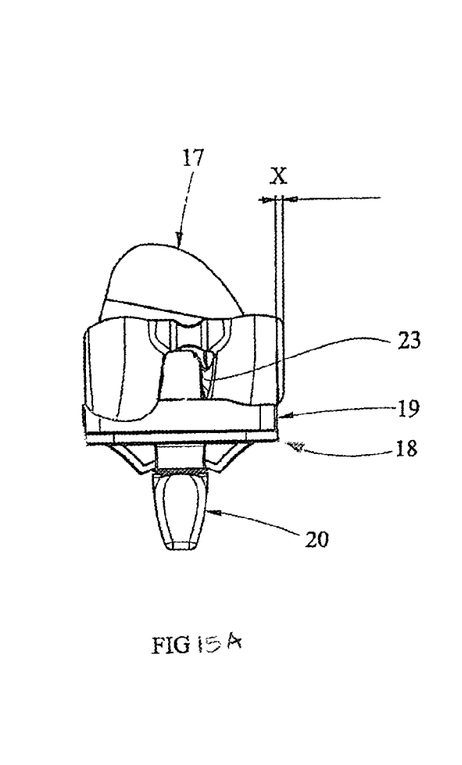
FIGS. 15A and 15B show respective rear views of a prosthesis in accordance with an embodiment of the present invention, in both fully extended and fully flexed states of the knee.
Figure 15B:
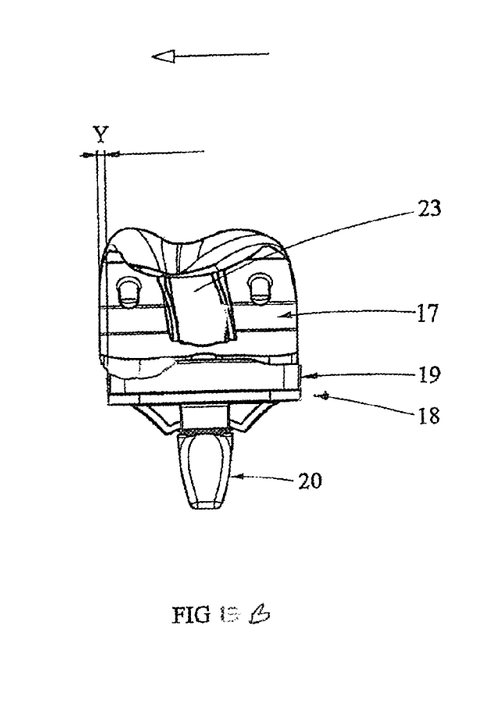

FIGS. 15A and 15B show the assembled knee prosthesis in fully extended and fully flexed states of the knee, in use. Typically, there is lateral translatory movement of the femur upon the tibia to the extent shown, i.e. with a lateral shift of 3.5 mm per 90°. These Figures show the respective overhangs X and Y at the respective opposite sides of the prosthesis in the fully extended and fully flexed states respectively.

Posterior Stabilised Design

Figure 16:
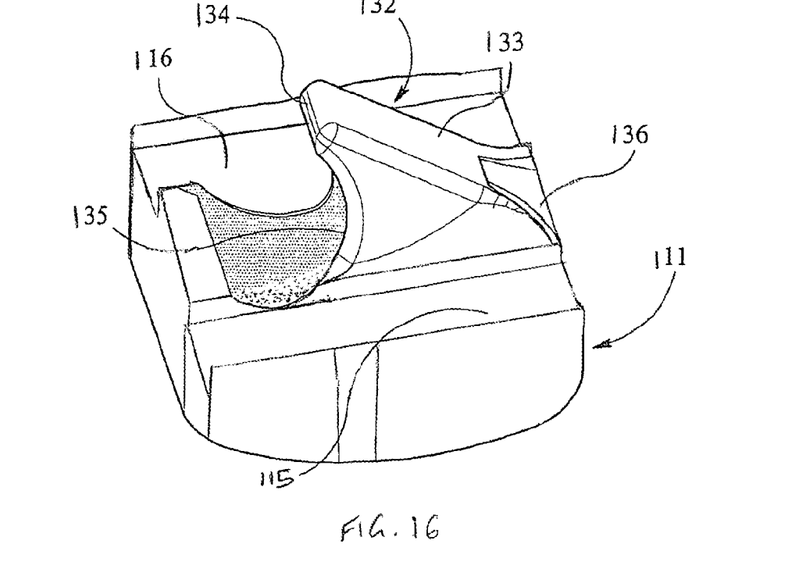
FIG. 16 shows a rear perspective view of another bearing component of a tibial component of a knee prosthesis according to embodiments of the present invention.
Figure 17:
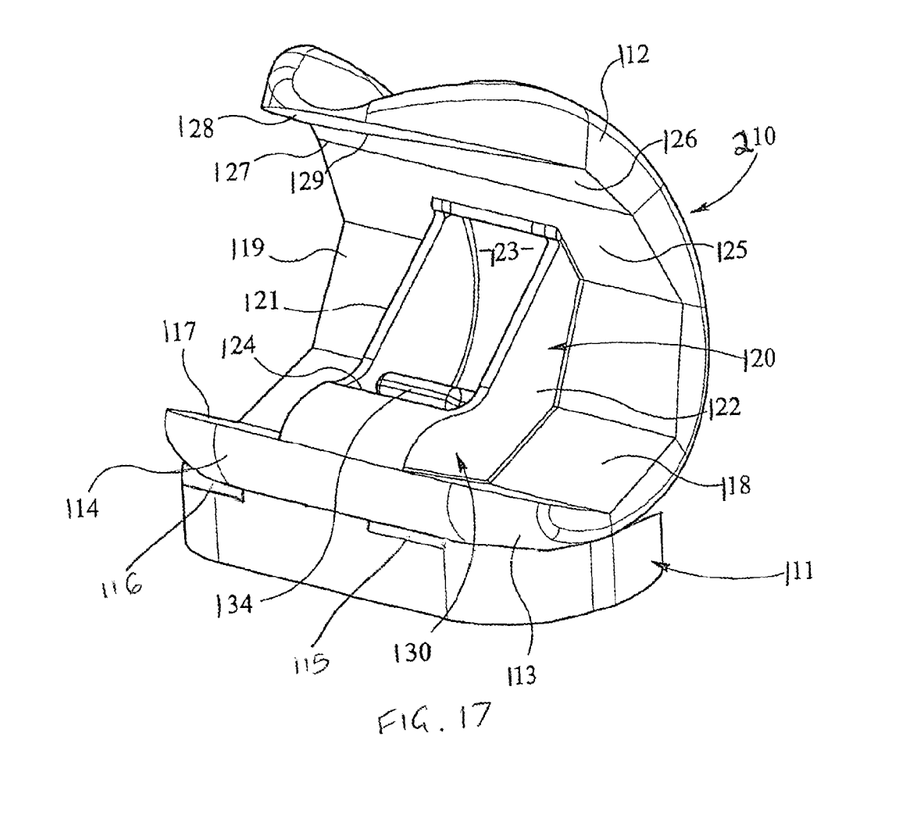
FIG. 17 shows a rear perspective view of the bearing component of FIG. 16 when engaged (via a cam and peg mechanism) with a femoral component for a knee prosthesis according to an embodiment of the present invention.

FIG. 16 shows a rear view of another bearing component 111 of a tibial component of a knee prosthesis according to another embodiment of the present invention and FIG. 17 shows a rear view of the bearing component 111 of FIG. 16 when engaged (via a cam 130 and peg 132 mechanism) with a femoral component 210.

The bearing component 111 has medial and lateral bearing surfaces 115, 116 which are similar in form to those illustrated in FIG. 7 but which are each squared off to forms angled troughs having a base and two perpendicular sidewalls. Thus, the bearing surfaces 115, 116 are configured to constrain helical condyles only in a medio-lateral direction and to allow unconstrained movement in an antero-posterior direction. Centrally of the component 111, but towards the slightly convex front peripheral side surface thereof is formed an upstanding peg 132, constituting a follower, with the opposite rear peripheral side surface of the bearing component being flat, with the peg 32 terminating short thereof.

As can be seen from FIG. 16, the peg 132 has a body which rises with an upwardly angled flat top surface 133 from the front side surface to form an arcuate downwardly extending front nose part 134. Below this part 134 is a cam follower surface constituted by a recess 135 which is of part-cylindrical concave form to match a cylindrical external surface of a rod 130 of the femoral component 210 so that, as will be described, rod 130 can engage in the recess 135 and follow the shape of the recess thereby allowing the femoral component 210 to move relative to the bearing component 111 during flexion of the knee. The recess 135 extends through approximately 180° from the surface of the bearing component 111 between the bearing surfaces 115, 116 to the lower edge of the front part 134. However the angle through which the recess 135 extends can be varied as required, and the respective shapes of the inter-engaging parts of the cam (rod 130) and the follower (peg 132) can also be varied as required. In the embodiment illustrated, there is also provided a lateralised recess 136 at the front side of the component 111 to accommodate a lateralised patella tendon.

With the arrangement shown in FIG. 17, where the femoral component 210 (which is largely as per the femoral component described above in relation to FIGS. 12A through 12C with the addition of the rod 130) is fitted on the bearing component 111, and the knee is unflexed, the helical condylar parts 113 and 114 of the femoral component 210 will have point contact engagement with the corresponding bearing surfaces 115, 116. As the knee is flexed, there is relative sliding movement between the femoral component 210 and the bearing component 111, as the respective exterior surfaces of the condylar parts 113, 114 slide over the corresponding bearing surfaces 115, 116 of the bearing component, with the knee flexing up to 90°. During this initial flexion, for example up to approximately 70°, the rod 130 remains clear of the inner surface of recess 135. This angle could be varied as required, and indeed in another embodiment there could be no engagement between the surface of recess 135 and the rod 130 until an angle of flexion of approximately 90° is reached. When the particular angle is reached, however, the rod 130 enters the recess 135 defined by the peg 132 and the matching of the external surface of the rod 130 with the internal surface of the recess 135 enables the relative sliding movement between the femoral component 210 and the bearing component 111 to continue with the femoral component 210 effectively being pulled back due to engagement of the rod 130 in the recess 135. Thus, contact is maintained beyond 90°, for example up to approximately 160° or whatever maximum flexion is with any given patient, due to the rod 130 engaging against and following the form of the interior surface of the recess 135, thereby allowing continued flexion of the knee. Furthermore, the fact that the condyles are unconstrained in the antero-posterior direction allows the femoral component 210 to move backwards as the rod 130 is engaged in the recess 135, without affecting the lateral translation of the femoral component due to the helical nature of the condyles and the correspondingly angled nature of the bearing surfaces 115, 116.

Some embodiments of the present invention can enable congruent contact to be maintained between at least one femoral condyle and the bearing component throughout a range of flexion of the knee, e.g. for at least 0-60°. The helical nature of the condyles has the effect of laterally displacing the patella groove. Moreover the form of the condyles upon movement, i.e. flexing, of the knee induce a lateral translatory movement of the femur upon the tibia with increasing flexion of the knee, thus further displacing laterally the patella groove. In addition, the fact that at least one of the condyles is unconstrained in at least an antero-posterior direction allows the femoral component to shift backwards with respect to the tibial component, without the need for a separate mobile bearing component.

As a consequence of the above, it will be appreciated that this knee replacement design more faithfully reproduces the natural position of the patella groove on the prosthetic femoral component, so that desired lateral patella tracking is more faithfully achieved, thereby reducing pain and morbidity. It will also be appreciated that this required tracking is achieved without any removal of the lateral femoral condyle and without the need for a mobile bearing component.

It will be appreciated by persons skilled in the art that various modifications may be made to the above embodiments without departing from the scope of the present invention. For example, features described in relation to one embodiment may be mixed and matched with features described in relation to one or more other embodiments.

The invention claimed is:

1. A knee prosthesis comprising:
   a femoral component for securement to a femur, the femoral component defining medial and lateral condyles and an intercondylar groove; and
   a tibial component for securement to a tibia, the tibial component having respective bearing surfaces shaped to engage with said condyles both when the knee, in use, is extended and also over a range of flexion;
   wherein the medial and lateral condyles are both part-helical in shape and the respective bearing surface for one of the condyles is correspondingly part-helical in at least a medio-lateral direction; and
   wherein the other bearing surface is incongruent with the other condyle in at least the antero-posterior direction so as to allow for antero-posterior movement of the femoral component relative to the bearing surfaces of the tibial component.

2. The knee prosthesis according to claim 1 wherein at least one of the condyles has point or line contact, as opposed to area contact, with a respective bearing surface.

3. The knee prosthesis according to claim 1 wherein at least the bearing surfaces of the tibial component comprise a cross-linked polymer.

4. The knee prosthesis according to claim 1 wherein at least one of the condyles is shaped in the manner of a thread on a screw, and the respective bearing surface is shaped in the manner of a thread cut in a complementary nut.

5. The knee prosthesis according to claim 1 wherein the medial condyle is configured for congruent contact with a respective bearing surface which is correspondingly part-helical, the congruent contact being in both the medio-lateral direction and the antero-posterior direction.

6. The knee prosthesis according to claim 1 wherein each of the bearing surfaces is configured for incongruent contact with the respective condyles in the antero-posterior direction so as to allow for the femoral component to freely slide back and forth on the tibial component during flexion and extension.

7. The knee prosthesis according to claim 6 wherein the respective bearing surfaces of both of the condyles are correspondingly part-helical in the medio-lateral direction.

8. The knee prosthesis according to claim 1 wherein at increasing flexion, a peg and cam mechanism are designed to engage to cause roll-back of the femoral component on the tibial component.

9. The knee prosthesis according to claim 1 wherein the transverse cross-section of each condyle is flat, curved or semi-spherical.

10. The knee prosthesis according to claim 1 wherein the transverse cross-section is different for each condyle.

11. The knee prosthesis according to claim 1 wherein the tibial component comprises a bearing component comprising the bearing surfaces and an engaging component comprising an engagement feature for securing the tibial component to a patient's tibia.

12. The knee prosthesis according to claim 11 wherein the bearing component is configured for snap-fit engagement with the engaging component.

13. The knee prosthesis according to claim 11 wherein the bearing component is formed from a cross-linked polymer.

14. The knee prosthesis according to claim 1 wherein flexion of the knee, in use, from an extended position induces lateral translatory movement of the femoral component upon the tibial component.

15. A knee prosthesis comprising:
   a femoral component for securement to a femur, the femoral component defining medial and lateral condyles and an intercondylar groove; and
   a tibial component for securement to a tibia, the tibial component having respective bearing surfaces shaped to engage with said condyles both when the knee, in use, is extended and also over a range of flexion;
   one of the condyles being part-helical in shape and the respective bearing surface of the tibial component being correspondingly part-helical in at least a medio-lateral direction;
   wherein the other bearing surface is incongruent with the other condyle in at least the antero-posterior direction so as to allow for antero-posterior movement of the femoral component relative to the bearing surfaces of the tibial component; and
   wherein each of the bearing surfaces is configured for incongruent contact with the respective condyles in the antero-posterior direction so as to allow for the femoral component to freely slide back and forth on the tibial component during flexion and extension.

16. The knee prosthesis according to claim 15 wherein the other condyle is part-helical and the respective bearing surface is similarly helical in the medio-lateral direction.

17. The knee prosthesis according to claim 15 wherein the other condyle is non-helical and the respective bearing surface does not constrain the movement of the other condyle in the medio-lateral direction.

* * * * *